(12) United States Patent
Thirumalai Rajan et al.

(10) Patent No.: US 10,544,189 B2
(45) Date of Patent: Jan. 28, 2020

(54) PROCESS FOR THE PREPARATION OF (2S)-N-((S)-1-((S)-4-METHYL-1-((R)-2-METHYL OXIRAN-2-YL)-1-OXOPENTAN-2-YLCARBAMOYL)-2-PHENYLETHYL)-2-((S)-2-(2-MORPHOLINOACETAMIDO)-4-PHENYLBUTANAMIDO)-4-METHYL-PENTANAMIDE

(71) Applicant: MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Venkat Reddy Ghojala, Telangana (IN); Laxmi Reddy Katta, Telangana (IN)

(73) Assignee: MSN LABORATORIES PRIVATE LIMITED, Hyderabad, Telangana (IN)

(*) Notice: Subject to any disclaimer, the term of this patent is extended or adjusted under 35 U.S.C. 154(b) by 0 days.

(21) Appl. No.: 15/568,392

(22) PCT Filed: Apr. 22, 2016

(86) PCT No.: PCT/IN2016/000105
§ 371 (c)(1),
(2) Date: Oct. 20, 2017

(87) PCT Pub. No.: WO2016/170544
PCT Pub. Date: Oct. 27, 2016

(65) Prior Publication Data
US 2018/0298056 A1 Oct. 18, 2018

(30) Foreign Application Priority Data

Apr. 22, 2015 (IN) .......................... 2054/CHE/2015
Jun. 1, 2015 (IN) .......................... 2740/CHE/2015

(51) Int. Cl.
*C07K 5/103* (2006.01)
*C07K 5/087* (2006.01)
*C07K 5/107* (2006.01)
*C07K 5/10* (2006.01)
*C07K 5/065* (2006.01)

(52) U.S. Cl.
CPC ........ *C07K 5/1008* (2013.01); *C07K 5/06078* (2013.01); *C07K 5/0812* (2013.01); *C07K 5/10* (2013.01); *C07K 5/1016* (2013.01)

(58) Field of Classification Search
CPC .. C07K 5/1008; C07K 5/0812; C07K 5/1016; C07K 5/06078; C07K 5/10
See application file for complete search history.

(56) References Cited

U.S. PATENT DOCUMENTS 8,207,297 B2 * 6/2012 Smyth ................. C07K 5/0812
530/330

FOREIGN PATENT DOCUMENTS

| CN | 103804469 | 5/2014 |
| CN | 104086624 | 10/2014 |
| WO | WO 2006/017842 | 2/2006 |

OTHER PUBLICATIONS

El-Faham et al (Chem.Rev., 2011,111, 6557-6602) (Year: 2011).*
International Search Report issued in International Patent Application No. PCT/IN2016/000105, dated Dec. 9, 2016.

* cited by examiner

*Primary Examiner* — Sudhakar Katakam
(74) *Attorney, Agent, or Firm* — IP Pundit LLC

(57) ABSTRACT

The present invention relates to process for the preparation of (2S)-N-((S)-1-((S)-4-methyl-1-((R)-2-methyloxiran-2-yl)-1-oxopentan-2-ylcarbamoyl)-2-phenyethyl)-2-((S)-2-(2-morpholinoacetamido)-4-phenylbutanamido)-4-methylpentanamide represented by the following structural formula-1.

Formula-1

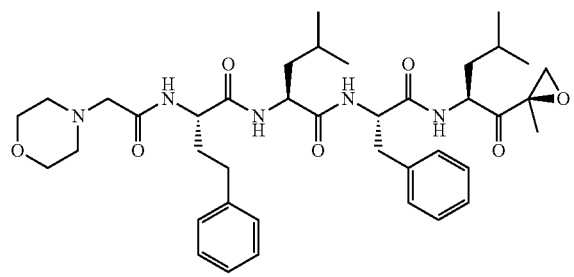

5 Claims, No Drawings

PROCESS FOR THE PREPARATION OF (2S)-N-((S)-1-((S)-4-METHYL-1-((R)-2-METHYL OXIRAN-2-YL)-1-OXOPENTAN-2-YLCARBAMOYL)-2-PHENYLETHYL)-2-((S)-2-(2-MORPHOLINOACETAMIDO)-4-PHENYL-BUTANAMIDO)-4-METHYLPENTANAMIDE

RELATED APPLICATIONS

This application is a national phase application under 35 U.S.C. § 371 of International Application No. PCT/IN2016/000105, filed on Apr. 22, 2016, which claims priority to claims the benefit of priority of our Indian patent application 2054/CHE/2015 filed on Apr. 22, 2015 and 2740/CHE/2015 filed on Jun. 1, 2015; the disclosure of which are incorporated herein by reference in their entirety.

FIELD OF THE INVENTION

The present invention provides process for the preparation of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide represented by the following structural formula-1.

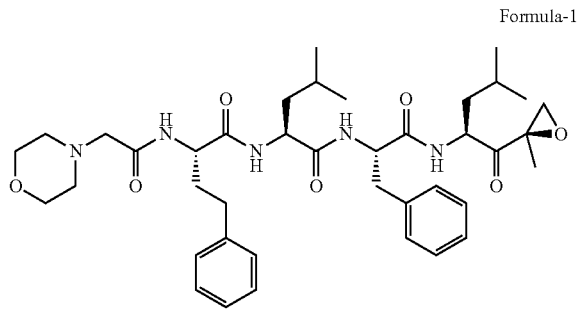 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Formula-1

The present invention also provides intermediate compounds which are useful for the preparation of compound of formula-1.

BACKGROUND OF THE INVENTION (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide, commonly known as Carfilzomib is an anticancer drug acting as a selective proteasome inhibitor which is indicated for the treatment of patients with multiple myeloma who have received at least two prior therapies including Bortezomib and an immunomodulatory agent. It is a tetrapeptide epoxyketone and an analog of Epoxomicin.

U.S. Pat. No. 7,417,042B2 has described Carfilzomib, its analogous compounds and also process for their preparation.

BRIEF DESCRIPTION OF THE INVENTION

The first aspect of the present invention is to provide process for the preparation of (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide compound of formula-1.

The second aspect of the present invention is to provide novel intermediate compounds which are useful in the preparation of compound of formula-1.

The third aspect of the present invention is to provide process for the preparation of (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide compound of formula-1.

The fourth aspect of the present invention is to provide process for the preparation of amorphous form of compound of formula 1.

DETAILED DESCRIPTION OF THE INVENTION

The term "suitable solvent" used in the present invention refers to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, t-butanol, ethane-1,2-diol, propane-1,2-diol and the like; "polar solvents" such as water; formic acid, acetic acid or mixture of any of the aforementioned solvents.

The term "suitable base" used in the present invention refers to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropyl mine, diisopropylethylamine, diisobutylamine, triethylamine, triisopropyl amine, tributylamine, tert. butyl amine, pyridine, 4-dimethylaminopyridine (DMAP), imidazole, N-methyl imidazole, 1,8-diazabicyclo[5.4.0]undec-7-ene (DBU), 1,5-diazabicyclo[4.3.0]non-5-ene (DBN), N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

The term "suitable acid" used in the present invention refers to hydrochloric acid, hydrobromic acid, nitric acid, sulfuric acid, phosphoric acid, formic acid, acetic acid, trifluoroacetic acid, alkyl/aryl sulfonic acids such as methane sulfonic acid, ethane sulfonic acid, benzenesulfonic acid, p-toluenesulfonic acid and the like.

In the present invention, the amine protecting groups 'P₁' & 'P₂' are selected from but not limited to tert-butyloxycarbonyl (Boc), benzyloxycarbonyl (Cbz), 9-fluorenylmethyloxy carbonyl (Fmoc), benzyl (Bn), carbamate group, p-methoxyphenyl (PMP), p-methoxybenzyl (PMB), 3,4-dimethoxy benzyl (DMPM), trityl (Tr), alkyl/aryl sulfonyl such as methanesulfonyl, ethanesulfonyl, benzenesulfonyl, toluenesulfonyl and the like; acyl groups such as acetyl (Ac), trifluoroacetyl (TFA), benzoyl (Bz) group and the like.

The suitable amine protecting agent is selected such that it is capable of protecting the nitrogen atom with any of the above mentioned amine protecting groups.

Suitable amine protecting agent is selected from but not limited to di-tert.butyl dicarbonate (DIBOC), benzyl chloroformate, fluorenylmethyloxy carbonyl chloride (FMOC chloride), trityl chloride, acetyl chloride, acetic anhydride, trifluoroacetic acid, trifluoroacetic anhydride, benzoyl halides, benzyl halides, alkyl/arylsulfonic acids/acid halides/anhydrides such as methanesulfonyl chloride, ethanesulfonyl chloride, benzenesulfonyl chloride, toluenesulfonyl chloride, methanesulfonic acid, ethanesulfonic acid, p-toluenesulfonic acid, p-toluenesulfonic anhydride and the like; alkyl trifluoroacetates such as methyl trifluoroacetate, ethyl trifluoroacetate, isopropyl trifluoroacetate, vinyl trifluoroacetate; trifluoroacetic acid, trifluoroacetyl chloride and the like.

The suitable deprotecting agent is selected based on the protecting group employed. The suitable deprotecting agent is selected from but not limited to acids such as hydrochloric acid, hydrobromic acid, sulfuric acid, nitric acid, aq.phosphoric acid, trifluoroacetic acid, methane sulfonic acid, p-toluenesulfonic acid and the like; acetyl chloride in combination with alcohols; bases such as alkali metal hydroxides, alkali metal alkoxides, alkali metal carbonates, cesium carbonate/imidazole, ammonia, cerium(IV) ammonium nitrate (CAN); organic bases such as methylamine, ethylamine, diethylamine, triethylamine, piperidine and the like; hydrogenating agents such as Pd/C, Pd(OH)₂/C (Pearlman's catalyst), palladium acetate, platinum oxide, platinum black, sodium borohydride, Na-liquid ammonia, Raney-Ni, tri($C_1$-$C_6$)alkylsilanes, tri($C_1$-$C_6$)alkylsilyl halides and the like.

The first aspect of the present invention provides process for the preparation of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide compound of formula-1, comprising of;
a) Reacting the (S)-2-((S)-4-methyl-2-((S)-2-(2-morpholinoacetamido)-4-phenyl butanamido)pentanamido)-3-phenylpropanoic acid compound of formula-2

Formula-2

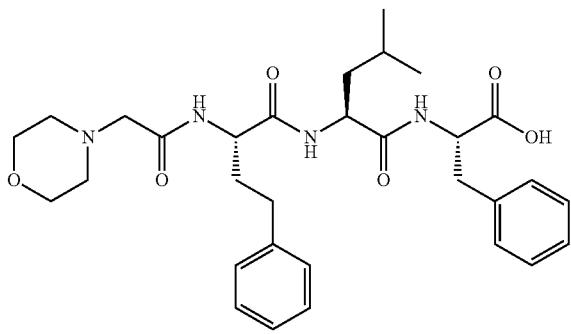

with compound of general formula $R_1$—OH in a suitable solvent optionally in presence of a suitable coupling agent and/or suitable base to provide compound of general formula-3, Formula-3

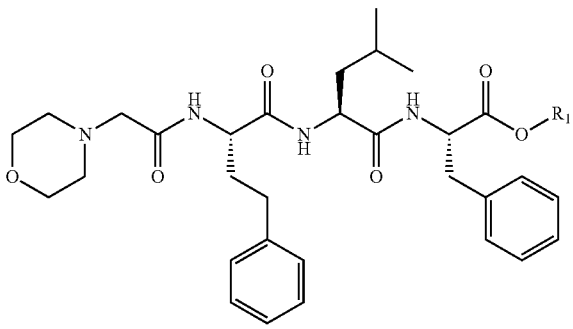

b) optionally isolating the compound of general formula-3 from the reaction mixture as a solid,
c) reacting the compound of general formula-3 with (S)-2-amino-4-methyl-1-((R)-2-methyloxiran-2-yl)pentan-1-one compound of formula-4 or its acid-addition salt Formula-4

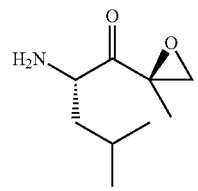

in a suitable solvent optionally in presence of a suitable base to provide compound of formula-1.

Wherein, the group '$R_1$' represents $C_1$-$C_6$ straight chain or branched chain alkyl group, substituted/unsubstituted $C_6$-$C_{10}$ aryl/aralkyl group; aliphatic group such as alkylsulfonyls; substituted/unsubstituted arylsulfonyl such as benzenesulfonyl, p-toluenesulfonyl and the like; aromatic groups selected from but not limited to substituted or unsubstituted aryl/aralkyl having one or more similar or different substituents selected from hydroxy, halogens, $NO_2$, $NH_2$, alkylamino, arylamino, alkoxy, aryloxy, cyano, sulfonic acid, $SCH_3$, $SO_2CH_3$, $SO_2NH_2$ and the like. '$R_1$' also represents the following groups selected from

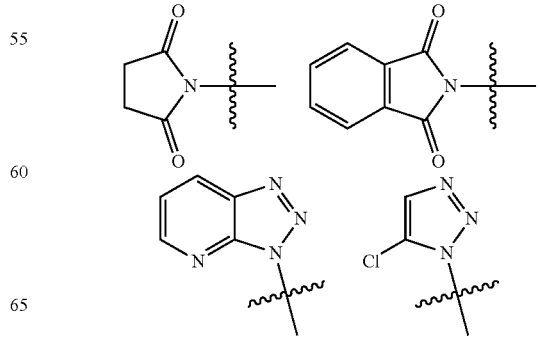

From step-a) to step-c) the suitable base and the suitable solvent are same as defined above in the specification;

In step-a) the suitable coupling agent is selected from but not limited to N,N'-dicyclohexylcarbodiimide (DCC), N,N'-diisopropylcarbodiimide (DIC), 1-ethyl-3-(3-dimethylaminopropyl)carbodiimide hydrochloride (EDC.HCl), 1-[bis(dimethylamino) methylene]-1H-1,2,3-triazolo[4,5-b]pyridinium 3-oxid hexafluorophosphate (HATU), 2-(1H-benzotriazol-1-yl)-1,1,3,3-tetramethyluronium hexafluorophosphate (HBTU), 1H-benzo triazolium 1-[bis(dimethylamino)methylene]-5chloro-hexafluorophosphate (1-) 3-oxide (HCTU), alkyl or aryl chloroformates such as ethyl chloroformate, benzylchloroformate, diphenylphosphoroazidate (DPPA), thionyl chloride, oxalyl chloride, phosphorous oxychloride, phosphorous pentachloride, 4-methyl-2-oxopentanoyl chloride (i-BuCOCOCl), (benzotriazol-1-yloxy)tris(dimethylamino)phosphonium hexafluorophosphate (BOP), benzotriazol-1-yl-oxytripyrrolidinophosphonium hexafluorophosphate (PyBOP), methane sulfonyl chloride and the like optionally in combination with 1-hydroxy-7-azatriazole (HOAt), 1-hydroxybenzotriazole (HOBt), 1-hydroxy-1H-1,2,3-triazole-4-carboxylate (HOCt), O-(benzotriazol-1-yl)-N,N,N',N'-tetramethyluronium tetrafluoroborate (TBTU), N-hydroxysuccinamide (HOSu), N-hydroxysulfosuccinimide (Sulfo-NHS) and the like.

The reaction of compound of general formula-3 with compound of formula-4 or its acid addition salt as described in step-c) of the above process can also be carried out in presence of alkali metal halide or alkaline earth metal halide or metal halide or metal salt in a suitable solvent optionally in presence of suitable base to provide compound of formula-1.

Wherein, the alkali metal halide is selected from but not limited to LiCl, LiBr, LiI, NaBr, NaI, KBr, KI, CsCl, CsBr, CsI and the like; alkaline earth metal halide is selected from but not limited to $BeCl_2$, $BeBr_2$, $MgCl_2$, $MgBr_2$, $MgI_2$, $CaCl_2$, $CaBr_2$, $CaI_2$, $BaCl_2$, $BaBr_2$, $BaI_2$ and the like; metal halide is selected from but not limited to Zinc chloride, Zinc bromide, Zinc iodide, Copper chloride, Copper bromide, Copper iodide; metal salts of Fe, La, Yb; $Cu(OTf)_2$, $Cu(OAc)_2$, Copper sulfate and the like. Metal salts include halides, OTf salts and acetates.

The suitable base and the suitable solvent are same as defined above in the specification.

In the above aspect, the preparation of compound of general formula-3 can also be carried out by reacting the compound of formula-2 with compound of general formula $R_1$—OH in presence of an acid such as HCl, conc.$H_2SO_4$, trifluoroacetic acid, alky/aryl sulfonic acid such as methanesulfonic acid, p-toluenesulfonic acid and the like in a suitable solvent.

A preferred embodiment of the present invention provides process for the preparation of (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide compound of formula-1, comprising of;
a) Reacting the (S)-2-((S)-4-methyl-2-((S)-2-(2-morpholinoacetamido)-4-phenyl butanamido)pentanamido)-3-phenylpropanoic acid compound of formula-2 with 2,3,4,5,6-pentafluoro phenol in a suitable solvent optionally in presence of a suitable coupling agent and/or a base to provide (S)-perfluorophenyl 2-((S)-4-methyl-2-((S)-2-(2-morpholinoacetamido)-4-phenylbutanamido)pentanamido)-3-phenylpropanoate compound of formula-3a,

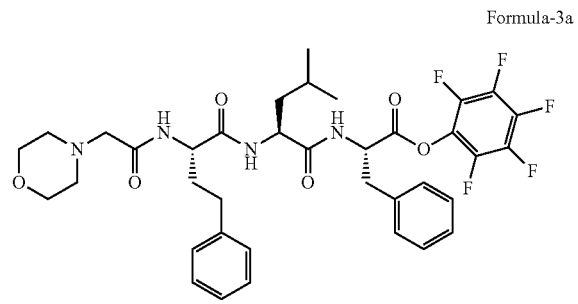 [SMILES: CC(C)C[C@H](NC(=O)[C@H](CCc1ccccc1)NC(=O)CN1CCOCC1)C(=O)N[C@@H](Cc1ccccc1)C(=O)Oc1c(F)c(F)c(F)c(F)c1F]

Formula-3a b) optionally isolating the compound of formula-3a as a solid,
c) reacting the compound of formula-3a with (S)-2-amino-4-methyl-1-((R)-2-methyloxiran-2-yl)pentan-1-one compound of formula-4 or its acid-addition salt in a suitable solvent optionally in presence of a suitable base to provide compound of formula-1.

Another preferred embodiment of the present invention provides a process for the preparation of (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide compound of formula-1, comprising of;
a) Reacting (S)-2-((S)-4-methyl-2-((S)-2-(2-morpholinoacetamido)-4-phenyl butanamido) pentanamido)-3-phenylpropanoic acid compound of formula-2 with N-hydroxy succinimide in a suitable solvent optionally in presence of a suitable coupling agent and/or a suitable base to provide (S)-2,5-dioxopyrrolidin-1-yl 2-((S)-4-methyl-2-((S)-2-(2-morpholinoacetamido)-4-phenylbutanamido)pentanamido)-3-phenyl propanoate compound of formula-3b,

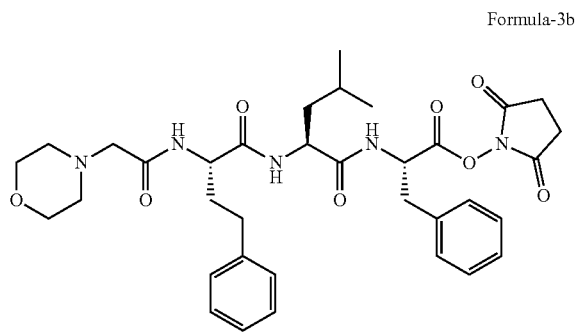 [SMILES: CC(C)C[C@H](NC(=O)[C@H](CCc1ccccc1)NC(=O)CN1CCOCC1)C(=O)N[C@@H](Cc1ccccc1)C(=O)ON1C(=O)CCC1=O]

Formula-3b b) optionally isolating the compound of formula-3b as solid,
c) reacting the compound of formula-3b with (S)-2-amino-4-methyl-1-((R)-2-methyloxiran-2-yl)pentan-1-one compound of formula-4 or its acid-addition salt in a suitable solvent optionally in presence of a suitable base to provide compound of formula-1.

A more preferred embodiment of the present invention provides process for the preparation of (2S)-N-((S)-1-((S)-4-methyl-1-((R)-2-methyloxiran-2-yl)-1-oxopentan-2-yl carbamoyl)-2-phenylethyl)-2-((S)-2-(2-morpholinoacetamido)-4-phenylbutanamido)-4-methylpentanamide compound of formula-1, comprising of;
a) Reacting (S)-2-((S)-4-methyl-2-((S)-2-(2-morpholinoacetamido)-4-phenylbutanamido) pentanamido)-3-phenyl-propanoic acid compound of formula-2 with 2,3,4,5,6-pentafluoro phenol in presence of N,N,N,N-tertramethyl O-(7-azabenzotriazol-1-yl)-uronium hexafluorophosphate, 1-hydroxybenzotriazole and N-methylmorpholine in dichloromethane to provide (S)-perfluorophenyl 2-((S)-4-methyl-2-((S)-2-(2-morpholino acetamido)-4-phenylbutanamido)pentanamido)-3-phenylpropanoate compound of formula-3a, Formula-3a

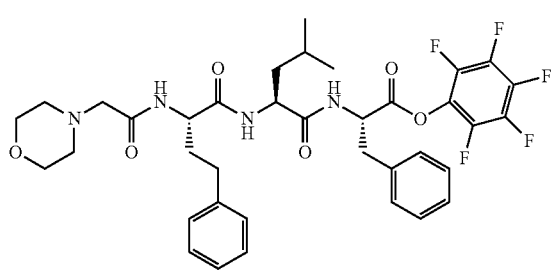

b) isolating the compound of formula-3a as a solid, c) reacting the compound of formula-3a with (S)-2-amino-4-methyl-1-((R)-2-methyloxiran-2-yl)pentan-1-one compound of formula-4 in dichloromethane to provide compound of formula-1.

The second aspect of the present invention provides novel intermediate compounds which are useful in the preparation of compound of formula-1. The said novel intermediate compounds are represented by the below mentioned structural formula

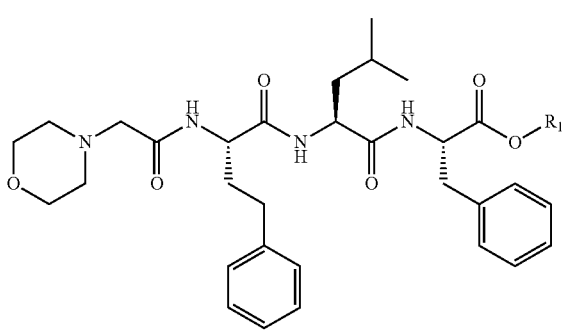

wherein, the group 'R₁' represents aliphatic group such as alkylsulfonyls; substituted/unsubstituted arylsulfonyl such as benzenesulfonyl, p-toluenesulfonyl and the like; aromatic groups selected from but not limited to substituted or unsubstituted aryl/aralkyl having one or more similar or different substituents selected from hydroxy, halogens, NO₂, NH₂, alkylamino, arylamino, alkoxy, aryloxy, cyano, sulfonic acid, SCH₃, SO₂CH₃, SO₂NH₂ and the like. 'R₁' also represents the following groups selected from

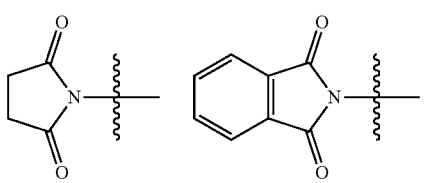

-continued

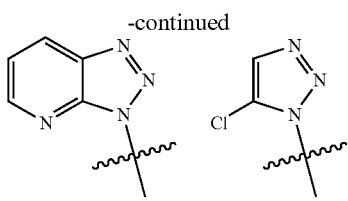

A preferred embodiment of the present invention provides novel intermediate compounds which are useful in the preparation of compound of formula-1. The said novel intermediate compounds are represented by the below mentioned structural formulae;

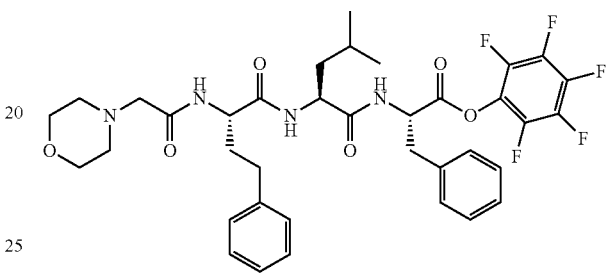

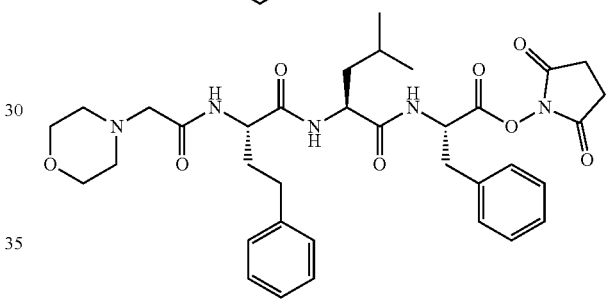

The above intermediate compounds are prepared by the present inventors and isolated from the reaction mixture in the form of pure solids, which in turn were useful in the preparation of pure compound of formula-1.

The third aspect of the present invention provides a process for the preparation of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide compound of formula-1, comprising of reacting the compound of general formula-3, Formula-3

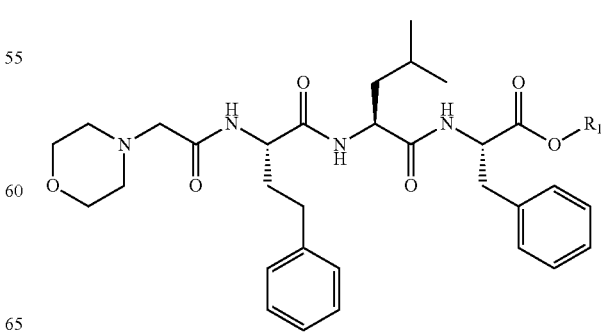

wherein, 'R' is as defined above;

with (S)-2-amino-4-methyl-1-((R)-2-methyloxiran-2-yl)pentan-1-one of formula-4 or its salt in suitable solvent optionally in presence of suitable base to provide compound of formula-1.

Wherein, the suitable base and the suitable solvent are same as defined in step-c) of the first aspect of the present invention.

A preferred embodiment of the present invention provides a process for the preparation of compound of formula-1, comprising of reacting the (S)-perfluorophenyl 2-((S)-4-methyl-2-((S)-2-(2-morpholinoacetamido)-4-phenylbutanamido)pentanamido)-3-phenylpropanoate compound of formula-3a with (S)-2-amino-4-methyl-1-((R)-2-methyloxiran-2-yl)pentan-1-one compound of formula-4 in dichloromethane to provide compound of formula-1.

In the above processes for the preparation of compound of formula-1, compound of general formula-3, formula-3a or formula-3b are preferably coupled with (S)-2-amino-4-methyl-1-((R)-2-methyloxiran-2-yl)pentan-1-one free base compound of formula-4.

The said compound of formula-4 is prepared by deprotecting the corresponding amine protected compound with a suitable deprotecting agent.

For example, the boc protected amine compound viz., tert.butyl ((S)-4-methyl-1-((R)-2-methyloxiran-2-yl)-1-oxopentan-2-yl)carbamate compound of formula-15 is treated with trifluoroacetic acid and the obtained compound is in-situ treated with a suitable base to direct provide free base compound of formula-4.

In one embodiment, the (S)-2-((S)-4-methyl-2-((S)-2-(2-morpholinoacetamido)-4-phenylbutanamido)pentanamido)-3-phenylpropanoic acid compound of formula-2 is prepared by the process as described in scheme-2 of the present invention.

An embodiment of the present invention provides an improved process for the preparation of (S)-2-((S)-4-methyl-2-((S)-2-(2-morpholinoacetamido)-4-phenylbutanamido) pentanamido)-3-phenylpropanoic acid compound of formula-2, comprising of;

a) Esterification of (S)-2-amino-3-phenylpropanoic acid compound of formula-5

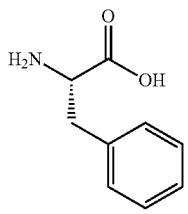

Formula-5 by treating it with a suitable esterification catalyst in a suitable solvent to provide corresponding ester compound of general formula-6 or its acid-addition salts,

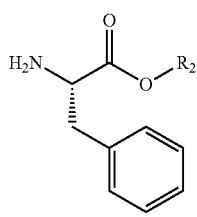

Formula-6 wherein, 'R$_2$' represents C$_1$-C$_6$ straight chain or branched chain alkyl group, substituted/unsubstituted C$_6$-C$_{10}$ aryl group;

b) reacting the compound of general formula-6 with compound of general formula-7

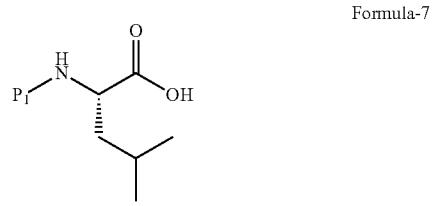

Formula-7 wherein, 'P$_1$' represents amine protecting group;
in a suitable solvent optionally in presence of a suitable coupling agent and/or a suitable base to provide compound of general formula-8,

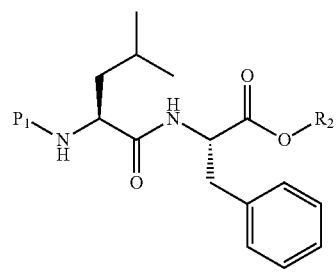

Formula-8 c) treating the compound of general formula-8 with a suitable deprotecting agent in a suitable solvent to provide compound of general formula-9 or its acid addition salts,

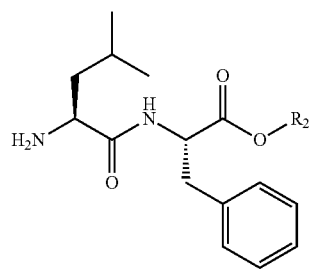

Formula-9 d) reacting the compound of general formula-9 with compound of general formula-10

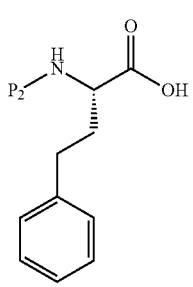

Formula-10 wherein, 'P$_2$' represents amine protecting group;

in a suitable solvent optionally in presence of a suitable coupling agent and/or a suitable base to provide compound of general formula-11, Formula-11

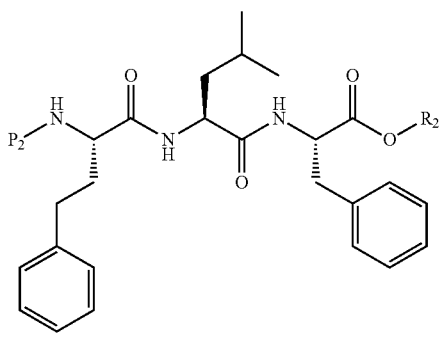

e) treating the compound of general formula-11 with a suitable deprotecting agent in a suitable solvent to provide compound of general formula-12 or its acid addition salts, Formula-12

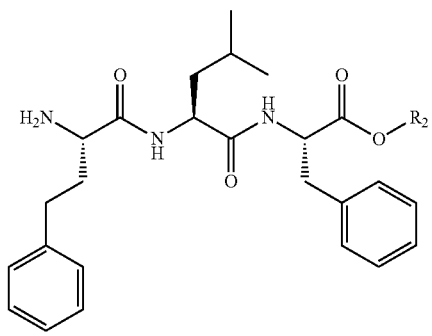

f) reacting the compound of general formula-12 with 2-morpholinoacetic acid compound of formula-13 or its acid-addition salt Formula-13

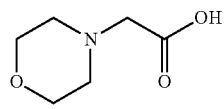

in a suitable solvent optionally in presence of a suitable coupling agent and/or a suitable base to provide compound of general formula-14, Formula-14

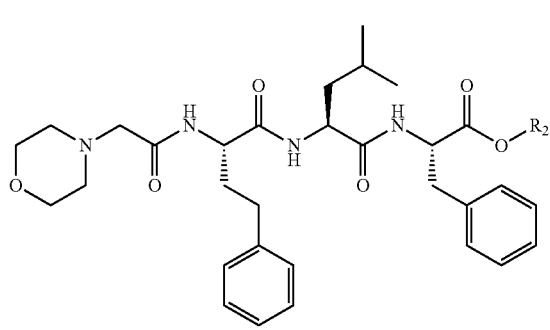

g) hydrolyzing the compound of general formula-14 in presence of a suitable base optionally in presence of a suitable solvent to provide compound of formula-2.

Wherein, in step-a) the suitable esterification catalyst is selected from thionyl chloride, conc. sulfuric acid, hydrochloric acid and the like;

In step-b), step-d) and step-f) the suitable coupling agent and suitable base are same as defined in step-a) of the first aspect of the present invention;

In step-c) & step-e) the suitable deprotecting agent is selected based on the protecting group employed and is same as defined above;

In step-g) the suitable base is selected from alkali metal hydroxides, alkali metal carbonates;

In step-a) to step-g) the suitable solvent wherever necessary is selected from hydrocarbon solvents, ether solvents, ester solvents, polar-aprotic solvents, chloro solvents, ketone solvents, nitrile solvents, alcohol solvents, polar solvents or their mixtures.

In the present invention, the amine protecting groups 'P$_1$' & 'P$_2$' are the same or different and independently represents amine protecting groups. In a preferred embodiment, 'P$_1$' & 'P$_2$' represents tert-butyloxycarbonyl (Boc) group.

In the present invention, when 'P$_1$' & 'P$_2$' represents tert-butyloxycarbonyl (Boc) group, the suitable deprotecting agent is selected from but not limited to HCl gas, aq.HCl, dry HCl, SOCl$_2$/methanol, ethyl acetate-HCl, methanol-HCl, ethanol-HCl, isopropyl alcohol-HCl, HCl/dioxane, diethylether-HCl, tri(C$_1$-C$_6$ alkyl)silyl chloride in presence of alcohol solvent, acetyl chloride/methanol, trifluoroacetic acid and the like.

A preferred embodiment of the present invention provides an improved process for the preparation of compound of formula-2, comprising of;

a) Esterification of (S)-2-amino-3-phenylpropanoic acid compound of formula-5 by treating it with thionyl chloride in methanol to provide (S)-methyl 2-amino-3-phenylpropanoate hydrochloride compound of formula-6a, Formula-6a

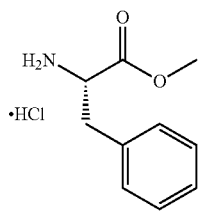

b) reacting the compound of formula-6a with (S)-2-((tert-butoxycarbonyl)amino)-4-methylpentanoic acid compound of formula-7a Formula-7a

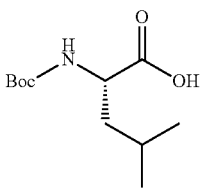

in presence of dicyclohexylcarbodiimide, 1-hydroxybenzotriazole and N-methylmorpholine in dichloromethane to provide (S)-methyl 2-((S)-2-(tert-butoxycarbonylamino)-4-methylpentanamido)-3-phenylpropanoate compound of formula-8a, Formula-8a

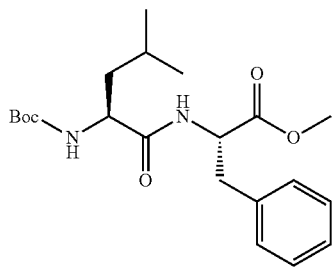

c) deprotecting the compound of formula-8a with isopropyl alcohol-HCl to provide (S)-methyl 2-((S)-2-amino-4-methylpentanamido)-3-phenylpropanoate hydrochloride compound of formula-9a, Formula-9a

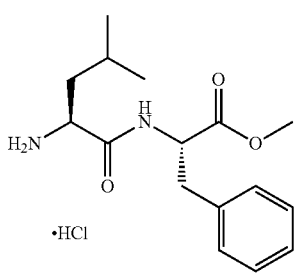

d) reacting the compound of formula-9a with (S)-2-((tert-butoxycarbonyl)amino)-4-phenyl butanoic acid compound of formula-10a Formula-10a

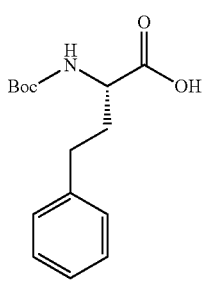

in presence of dicyclohexylcarbodiimide, 1-hydroxybenzotriazole and N-methylmorpholine in dichloromethane to provide (S)-methyl 2-((S)-2-tert.butoxycarbonylamino-4-phenylbutanamido-4-methylpentanamido)-3-phenyl propanoate compound of formula-11a, Formula-11a

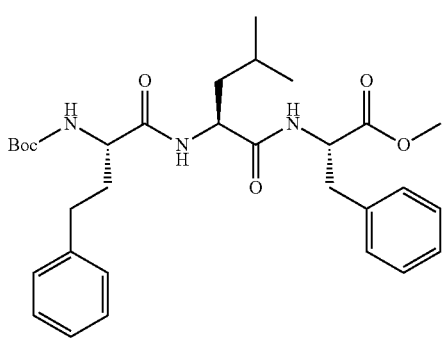

e) deprotecting the compound of formula-11a with ethyl acetate-HCl to provide (S)-methyl 2-((S)-2-amino-phenylbutanamido-4-methylpentanamido)-3-phenyl propanoate hydrochloride compound of formula-12a, Formula-12a

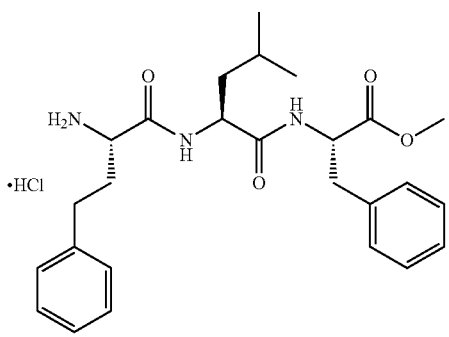

f) reacting the compound of formula-12a with 2-morpholinoacetic acid hydrochloride compound of formula-13a Formula-13a

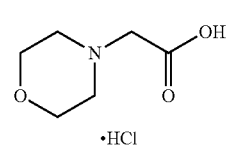

in presence of dicyclohexylcarbodiimide, 1-hydroxybenzotriazole and N-methyl morpholine in dichloromethane to provide (S)-methyl 2-((S)-4-methyl-2-((S)-2-(2-morpholinoacetamido)-4-phenylbutanamido) pentanamido)-3-phenylpropanoate compound of formula-14a, Formula-14a

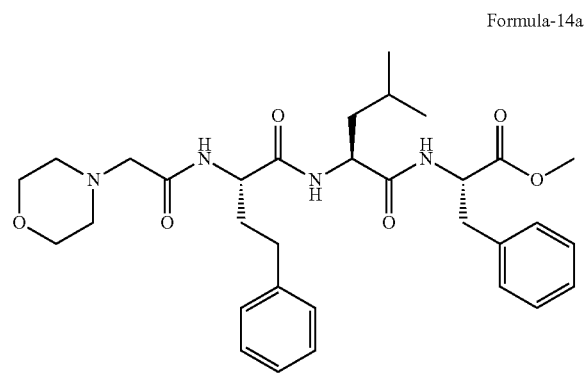 [SMILES: COC(=O)[C@H](Cc1ccccc1)NC(=O)[C@H](CC(C)C)NC(=O)[C@H](CCc1ccccc1)NC(=O)CN1CCOCC1]

g) hydrolyzing the compound of formula-14a in presence of lithium hydroxide monohydrate in a mixture of tetrahydrofuran and water to provide compound of formula-2.

U.S. Pat. No. 8,367,617B2 has described and characterized the amorphous form of compound of formula-1.

The fourth aspect of the present invention provides a process for the preparation of amorphous form of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide compound of formula-1, comprising of;

a) Providing a solution of compound of formula-1 in a suitable solvent or mixture of solvents, b) combining the solution with suitable anti-solvent at a suitable temperature to provide amorphous form of compound of formula-1.

Wherein, in step-a) the suitable solvent is selected from chloro solvents, alcohol solvents;

In step-b) the suitable anti-solvent is selected from hydrocarbon solvents; and the suitable temperature ranges from −70° C. to 70° C., preferably −60° C. to 50° C. and more preferably −40° C. to 30° C.

In the above process, the suitable solvent is preferably dichloromethane and the suitable anti-solvent is preferably n-pentane.

A preferred embodiment of the present invention provides a process for the preparation of amorphous form of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide compound of formula-1, comprising of;
a) Providing a solution of compound of formula-1 in dichloromethane,
b) combining the solution with n-pentane to provide amorphous form of compound of formula-1.

The compound of formula-2 and compound of formula-4 or its acid addition salt utilized in the above process can be synthesized by any of the known processes or they can be synthesized by the processes as described in the present invention.

The compounds of formulae-5, 7, 10 & 13 as utilized in the process described in scheme-2 of the present invention can be synthesized by any of the prior known processes.

By developing the above described process for the preparation of compound of formula-1, the present inventors were able to get the final API in excellent yield and quality with all the impurities and residual solvents controlled well within the limits as defined by ICH and most of the impurities in non-detectable level.

The (S)-2-((S)-4-methyl-2-((S)-2-(2-morpholinoacetamido)-4-phenylbutanamido)pentanamido)-3-phenylpropanoic acid compound of formula-2 (herein referred as "acid impurity") and diastereomer of compound of formula-1 (herein referred as "diastereomer impurity") have been formed as impurities during the synthesis of compound of formula-1. These impurities have been identified, characterized and well controlled within the limits as suggested by ICH guidelines.

The compound of formula-1 produced by the process of the present invention was analyzed by HPLC under the following conditions;
Apparatus: A liquid chromatographic system equipped with variable wavelength UV detector; Column: YMC pack Pro C18, 150×4.6 mm, S-3 μm, 12 nm; Flow rate: 1.0 mL/min; Column temperature: 30° C.; Auto sampler temperature: 5° C.; Wave length: 210 nm; Injection volume: 5 μL; Run time: 55 min; Elution: Gradient; Diluent: acetonitrile (100%); Buffer: Weigh accurately about 4.08 gm of potassium dihydrogen phosphate, 0.87 gm of dipotassium hydrogen phosphate and 3.0 gm of 1-octane sulfonic acid sodium salt anhydrous in 1000 mL of milli-Q-water, filter the solution through 0.22 μm Nylon membrane filter paper, Mobile phase-A: Buffer: acetonitrile (80:20 v/v); Mobile phase-B: Acetonitrile: water (90:10 v/v).

The compound of formula-1 produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The present invention is schematically represented as follows.

Scheme-1:

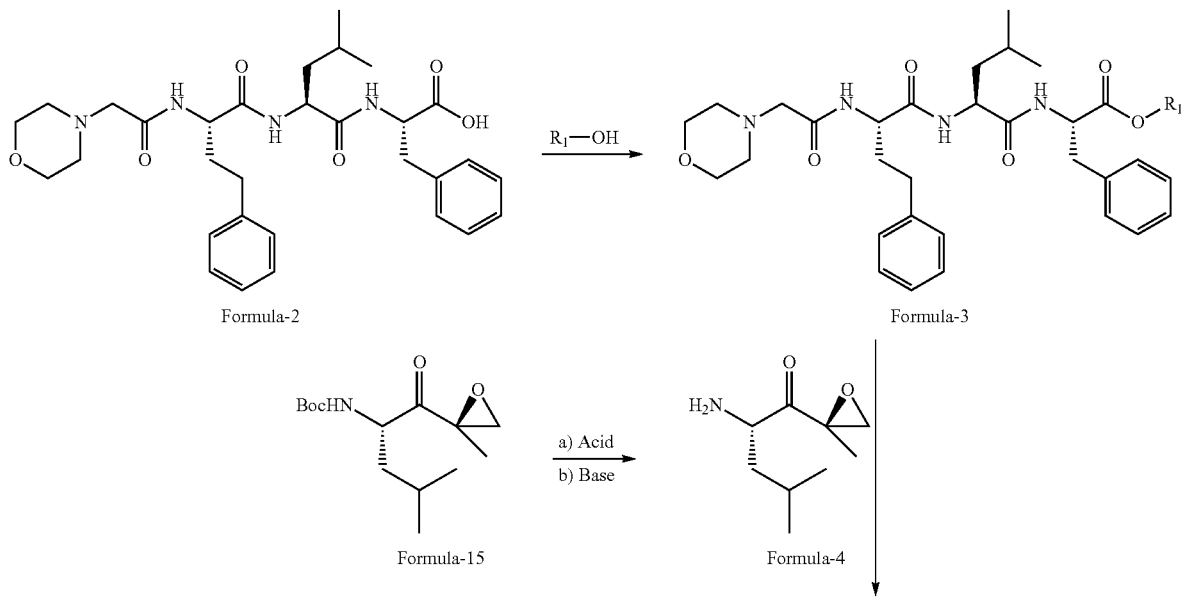

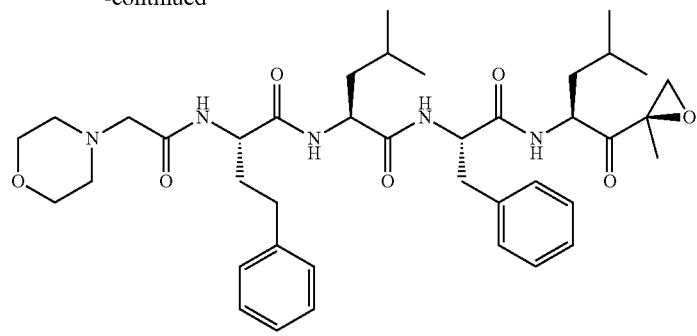
Carfilzomib
Formula-1
Wherein, 'R$_1$' is same as defined in the specification.
Scheme-II:
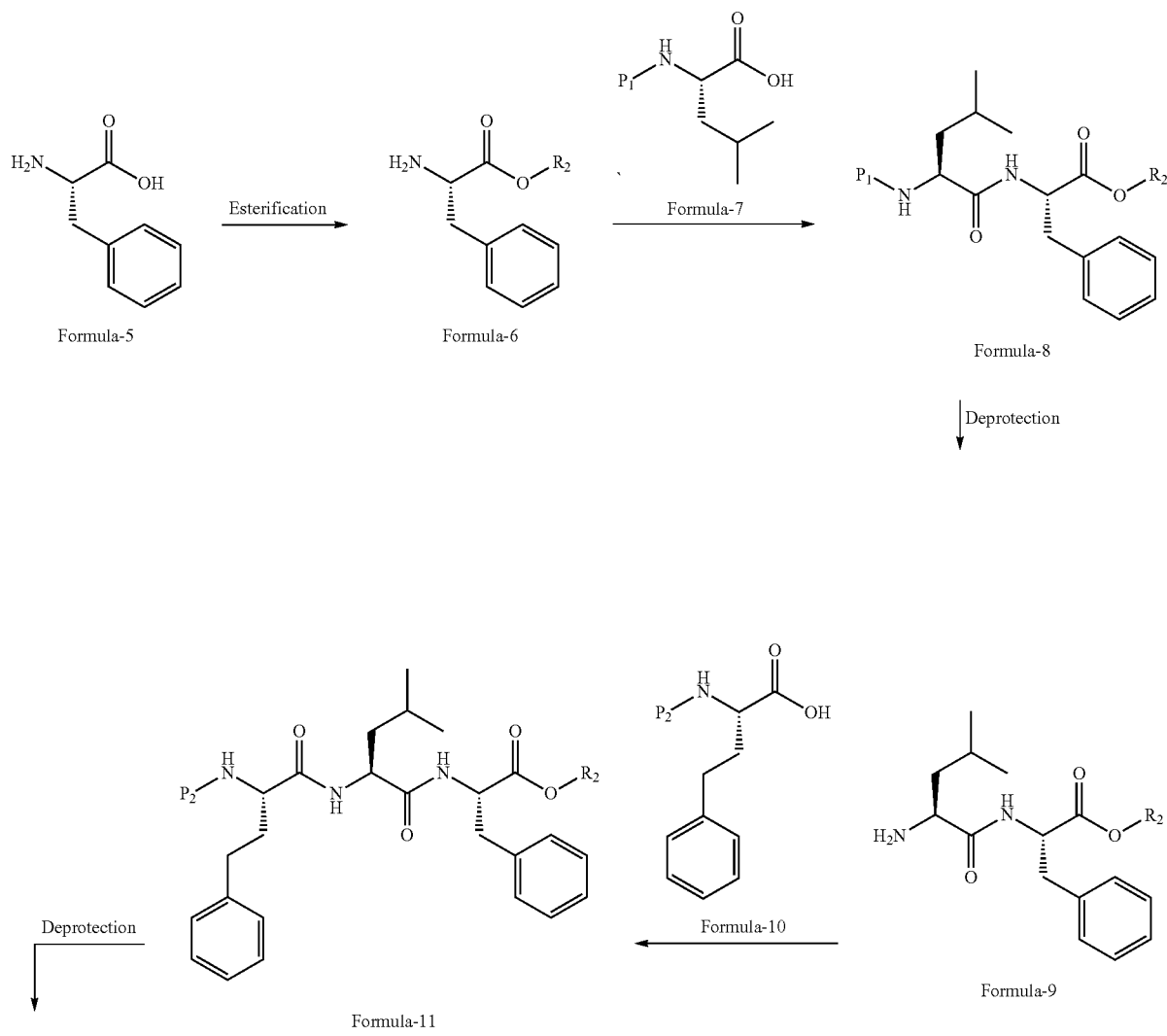

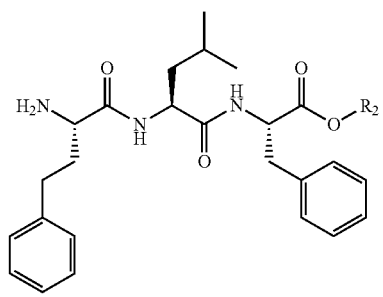 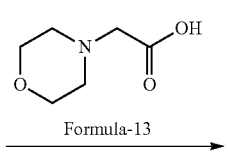 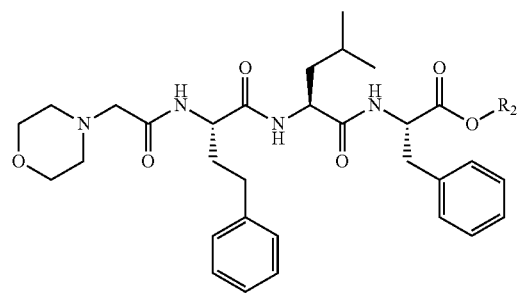

Formula-12    Formula-13    Formula-14

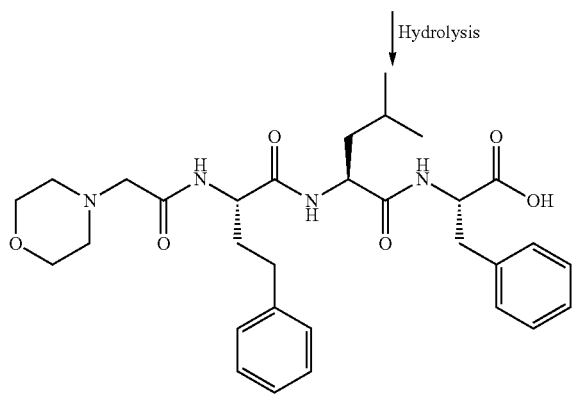

Formula-2

Wherein, 'R$_2$' represents C$_1$-C$_6$ straight chain or branched chain alkyl group, substituted/unsubstituted C$_6$-C$_{10}$ aryl group; 'P$_1$' & 'P$_2$' are the same or different and independently represents amine protecting groups as defined in the specification.

The best mode of carrying out the present invention is illustrated by the below mentioned examples. These examples are provided as illustration only and hence should not be construed as limitation to the scope of the invention.

EXAMPLES

Example-1: Preparation of (S)-methyl 2-amino-3-phenylpropanoate hydrochloride (Formula-6a)

Thionyl chloride (10.8 Kg) was slowly added to, a mixture of (S)-2-amino-3-phenylpropanoic acid compound of formula-5 (10 Kg) and methanol (50 Lt) at 25-30° C. and stirred the reaction mixture for 7 hrs at the same temperature. Distilled off the solvent completely from the reaction mixture under reduced pressure. Methyl tert.butyl ether (40 Lt) was added to the obtained compound at 25-30° C. and stirred the reaction mixture for 1 hr at the same temperature. Filtered the solid, washed with methyl tert.butyl ether and then dried the material to provide the title compound.

Yield: 13.06 Kg.

Example-2: Preparation of (S)-methyl 2-((S)-2-amino-4-methylpentanamido)-3-phenylpropanoate hydrochloride (Formula-9a)

1-Hydroxybenzotriazole (0.97 Kg) followed by N-methylmorpholine (7.32 Kg) were added to a pre-cooled mixture of (S)-methyl 2-amino-3-phenylpropanoate hydrochloride compound of formula-6a (7.76 Kg), (S)-2-((tert-butoxycarbonyl)amino)-4-methylpentanoic acid compound of formula-7a (9 Kg) and dichloromethane (63 Lt) at 0-5° C. under nitrogen atmosphere. A solution of dicyclohexylcarbodiimide (8.92 Kg) in dichloromethane (27 Lt) was slowly added to the reaction mixture at 0-5° C. Raised the temperature of the reaction mixture to 25-30° C. and stirred the reaction mixture for 90 min at the same temperature. Filtered the reaction mixture, washed with dichloromethane and then cooled the filtrate to 10-15° C. Aqueous sodium bicarbonate solution was slowly added to the filtrate at 10-15° C. and stirred the reaction mixture for 10 min at the same temperature. Both the organic and aqueous layers were separated and washed the organic layer with water. Distilled off the solvent completely from the organic layer under reduced pressure. Isopropyl alcohol (18 Lt) was added to the obtained compound at 25-30° C. Isopropyl alcohol-HCl (117 Lt) was slowly added lot wise to the reaction mixture at 25-30° C. and stirred the reaction mixture for 90 min at the same temperature. Filtered the precipitated solid, washed with methyl tert.butyl ether and then dried the material to provide the title compound.

Yield: 11.11 Kg.

Example-3: Preparation of (S)-methyl 2-((S)-2-amino-4-phenylbutanamido)-4-methylpentanamido)-3-phenylpropanoate hydrochloride (Formula-12a)

1-Hydroxybenzotriazole (0.82 Kg) and N-methylmorpholine (6.15 Kg) were slowly added to a pre-cooled mixture of (S)-methyl 2-((S)-2-amino-4-methylpentanamido)-3-phenylpropanoate hydrochloride compound of formula-9a (10

Kg), (S)-2-((tert-butoxycarbonyl)amino)-4-phenyl butanoic acid compound of formula-10a (9.33 Kg) and dichloromethane (70 Lt) at 0-5° C. under nitrogen atmosphere. A solution of dicyclohexylcarbodiimide (7.51 Kg) in dichloromethane (30 Lt) was slowly added to the reaction mixture at 0-5° C. Raised the temperature of the reaction mixture to 25-30° C. and stirred for 90 min at the same temperature. Filtered the reaction mixture and washed with dichloromethane. Aqueous sodium bicarbonate solution was slowly added to the pre-cooled filtrate at 10-15° C. and stirred the reaction mixture for 10 min at the same temperature. Both the organic and aqueous layers were separated and washed the organic layer with water. Distilled off the solvent completely from the organic layer under reduced pressure. Isopropyl alcohol (150 Lt) was added to the obtained compound at 25-30° C. Heated the reaction mixture to 80-85° C. and stirred for 1 hr at the same temperature. Cooled the reaction mixture to 25-30° C. and stirred for 1 hr at the same temperature. Filtered the solid and washed with methyl tert.butyl ether. The obtained compound was added to ethyl acetate (40 Lt) at 25-30° C. Ethyl acetate-HCl (130 Lt) was slowly added to the reaction mixture at 25-30° C. and stirred the reaction mixture for 90 min at the same temperature. Filtered the solid, washed with methyl tert.butyl ether and then dried the material to provide the title compound.

Yield: 13.31 Kg

Example-4: Preparation of (S)-2-((S)-4-methyl-2-((S)-2-(2-morpholinoacetamido)-4-phenylbutanamido)pentanamido)-3-phenylpropanoic acid (Formula-2)

1-Hydroxybenzotriazole (0.17 Kg) and N-methylmorpholine (1.24 Kg) were added to a pre-cooled mixture of (S)-methyl 2-((S)-2-amino-4-phenylbutanamido)-4-methyl-pentanamido)-3-phenylpropanoate hydrochloride compound of formula-12a (3 Kg), 2-morpholinoacetic acid hydrochloride compound of formula-13a (1.22 Kg) and dichloromethane (21 Lt) at 0-5° C. under nitrogen atmosphere. A solution of dicyclohexylcarbodiimide (1.51 Kg) in dichloromethane (9 Lt) was slowly added to the reaction mixture at 0-5° C. Slowly raised the temperature of the reaction mixture to 25-30° C. and stirred for 90 min at the same temperature. Filtered the reaction mixture and washed with dichloromethane. Cooled the filtrate to 10-15° C. and aqueous sodium bicarbonate solution was slowly added to it and stirred the reaction mixture for 10 min at the same temperature. Both the organic and aqueous layers were separated and washed the organic layer with dilute hydrochloric acid followed by with water. Distilled off the solvent completely form the organic layer under reduced pressure. Tetrahydrofuran (30 Lt) and water (15 Lt) were added to the obtained compound at 25-30° C. and cooled the reaction mixture to 10-15° C. A solution of lithium hydroxide monohydrate (0.51 Kg) in water (3 Lt) was added to the reaction mixture at 10-15° C. Raised the temperature of the reaction mixture to 25-30° C. and stirred for 2 hrs at the same temperature. Water and dichloromethane were added to the reaction mixture at 25-30° C. and stirred for 10 min at the same temperature. Both the organic and aqueous layers were separated and washed the aqueous layer with dichloromethane. Acidified the aqueous layer with aqueous hydrochloric acid solution at 25-30° C. and stirred the reaction mixture for 1 hr at the same temperature. Filtered the precipitated solid and washed with water. The obtained compound was added to methanol (18 Lt) at 25-30° C. Heated the reaction mixture to 55-60° C. and stirred for 45 min at the same temperature. Cooled the reaction mixture to 25-30° C. and stirred for 1 hr at the same temperature. Filtered the precipitated solid, washed with methanol and dried the material to provide the title compound.

Yield: 2.7 kg.

Example-5: Preparation of (S)-perfluorophenyl 2-((S)-4-methyl-2-((S)-2-(2-morpholino acetamido)-4-phenylbutanamido)pentanamido)-3-phenylpropanoate (Formula-3a)

1-Hydroxybenzotriazole (0.1 Kg) and N,N,N,N-tertramethyl O-(7-azabenzotriazol-1-yl)-uroniumhexafluorophosphate (1.49 Kg) were slowly added to a pre-cooled mixture of (S)-2-((S)-4-methyl-2-((S)-2-(2-morpholinoacetamido)-4-phenylbutanamido)pentanamido)-3-phenylpropanoic acid compound of formula-2 (2 Kg) and dichloromethane (40 Lt) at 10-15° C. A solution of 2,3,4,5,6-pentafluoro phenol (0.78 Kg) in dichloromethane (10 Lt) was added to the reaction mixture at 10-15° C. A solution of N-methylmorpholine (0.43 Kg) in dichloromethane (10 Lt) was slowly added to the reaction mixture at 10-15° C. and stirred the reaction mixture for 30 min at the same temperature. Aqueous sodium bicarbonate solution was slowly added to the reaction mixture at 10-15° C. Filtered the reaction mixture and washed with dichloromethane. Both the organic and aqueous layers were separated and washed the organic layer with water. Silica gel (10 Kg) was added to the organic layer at 25-30° C. and stirred the reaction mixture for 20 min at the same temperature. Filtered the reaction mixture through hyflow bed and washed the hyflow bed with dichloromethane. Distilled off the solvent completely form the filtrate and co-distilled with methyl tert.butyl ether. Methyl tert.butyl ether (20 Lt) was added to the obtained compound at 25-30° C. and stirred the reaction mixture for 40 min at the same temperature. Filtered the solid, washed with methyl tert.butyl ether and then dried the material to provide the title compound.

Yield: 1.73 Kg.

Example-6: Preparation of Compound of Formula-1

Tert.butyl ((S)-4-methyl-1-((R)-2-methyloxiran-2-yl)-1-oxopentan-2-yl)carbamate compound of formula-15 (0.56 Kg) was added to a pre-cooled mixture of dichloromethane (4.5 Lt) and trifluoroacetic acid (1.39 Kg) at 0-5° C. Raised the temperature of the reaction mixture to 25-30° C. and stirred for 2 hrs at the same temperature. Distilled the reaction mixture completely under reduced pressure. Dichloromethane (4.5 Lt) was added to the reaction mixture at 25-30° and cooled the reaction mixture to 10-15° C. Sodium carbonate (0.65 Kg) was slowly added to the reaction mixture at 10-15° C. and stirred the reaction mixture for 10 min at the same temperature. Filtered the reaction mixture and washed with dichloromethane. The filtrate was slowly added to a mixture of (S)-perfluorophenyl 2-((S)-4-methyl-2-((S)-2-(2-morpholinoacetamido)-4-phenylbutanamido)pentanamido)-3-phenyl propanoate compound of formula-3a (1.5 Kg) and dichloromethane (4.5 Lt) at 25-30° C. and stirred the reaction mixture for 2 hrs at the same temperature. Water was added to the reaction mixture at 25-30° C. and stirred the reaction mixture for 10 min at the same temperature. Both the organic and aqueous layers were separated and distilled off the solvent completely from the organic layer. The obtained compound is purified by silica gel column chromatography using methanol/dichloromethane mixture as eluent to get the title compound. Yield: 1.07 Kg.

Example-7: Purification of Compound of Formula-1

Compound of formula-1 (650 gm) was loaded in column with silica gel and eluted with acetonitrile/water mixture and discard the collected impure fractions. Eluted the column further with dichloromethane/methanol mixture and distilled off the solvent completely from the collected fractions under reduced pressure. The obtained compound was further purified by flash chromatography using n-hexane/isopropyl alcohol mixture as eluent and distilled off the solvent from the collected fractions under reduced pressure and co-distilled with dichloromethane. Dissolved the compound in dichloromethane, water was added to the obtained solution and stirred the reaction mixture for 5 min. Both the organic and aqueous layers were separated and distilled off the solvent completely from the organic layer under reduced pressure. Dichloromethane (5.2 Lt) and methanol (0.65 Lt) were added to the obtained compound at 25-30° C. and stirred the reaction mixture for 10 min at the same temperature. Distilled off the solvent completely from the reaction mixture under reduced pressure and dried the obtained material to provide pure compound of formula-1.

Yield: 536.2 gm.

Example-8: Preparation of Amorphous Form of Compound of Formula-1

A mixture of compound of formula-1 (500 gm) and dichloromethane (2000 ml) was stirred for 10 min at 25-30° C. to get a clear solution. Water (1500 ml) was added to the reaction mixture at 25-30° C. and stirred for 15 min at the same temperature. Both the organic and aqueous layers were separated and filtered the organic layer. The organic layer was slowly added to pre-cooled n-pentane (1500 ml) at −40° C. to −35° C. and stirred the reaction mixture for 90 min at the same temperature. Filtered the precipitated solid, washed with n-pentane and then dried the material to provide the title compound.

Purity by HPLC: 99.9%; Water content by KFR: 0.31% w/w;

Acid impurity: Not detected; Diastereomer impurity: Not detected; Highest individual unspecified impurity: 0.05%.

Particle size distribution (before micronization): D(0.1) is 24.0 μm; D(0.5) is 109.0 μm; D(0.9) is 229.0 μm.

Particle size distribution (after micronization): D(0.1) is 0.76 μm; D(0.5) is 2.01 μm; D(0.9) is 5.29 μm.

Example-9: Preparation of (S)-Methyl 2-amino-3-Phenylpropanoate Hydrochloride (Formula-6a)

Thionyl chloride (108 gm) was slowly added to a mixture of (S)-2-amino-3-phenylpropanoic acid compound of formula-5 (100 gm) and methanol (500 ml) at 25-30° C. and stirred the reaction mixture for 8 hrs at the same temperature. Distilled off the solvent completely from the reaction mixture under reduced pressure. Methyl tert.butyl ether (400 ml) was added to the obtained compound at 25-30° C. and stirred for 60 min at the same temperature. Filtered the solid, washed with methyl tert.butyl ether and then dried the material to get the title compound.

Yield: 117.2 gm; Purity by HPLC: 99.9%.

Example-10: Preparation of (S)-methyl 2-((S)-2-(tert-butoxycarbonylamino)-4-methylpentanamido)-3-phenylpropanoate (Formula-8a)

Hydroxybenzotriazole (10.8 gm) and N-methylmorpholine (81.2 gm) were added to a pre-cooled mixture of (S)-2-(tert-butoxycarbonylamino)-4-methylpentanoic acid compound of formula-7a (100 gm), (S)-methyl 2-amino-3-phenylpropanoate hydrochloride compound of formula-6a (86.2 gm) and dichloromethane (700 ml) at 0-5° C. under nitrogen atmosphere. A solution of dicyclohexylcarbodiimide (99.2 gm) in dichloromethane (300 ml) was slowly added to the reaction mixture at 0-5° C. Raised the temperature of the reaction mixture to 25-30° C. and stirred for 2 hrs at the same temperature. Filtered the reaction mixture, cooled the filtrate to 10-15° C. and washed with aqueous sodium bicarbonate solution followed by with aq.hydrochloric acid solution and then with water. Distilled off the solvent completely from the reaction mixture under reduced pressure. Methyl tert.butyl ether (200 ml) was added to the obtained compound, heated the reaction mixture to 50-55° C. and stirred for 10 min at the same temperature. n-Heptane (500 ml) was added to the reaction mixture at 50-55° C. Cooled the reaction mixture to 25-30° C. and stirred for 2 hrs at the same temperature. Filtered the precipitated solid, washed with n-heptane and then dried the material to get the title compound.

Yield: 133.8 gm; M.R: 70-75° C.; Purity by HPLC: 97%.

Example-11: Preparation of (S)-methyl 2-((S)-2-amino-4-methylpentanamido)-3-phenylpropanoate hydrochloride (Formula-9a)

Isopropyl alcohol-HCl (1000 ml) was slowly added to a mixture of (S)-methyl 2-((S)-2-(tert-butoxycarbonylamino)-4-methylpentanamido)-3-phenylpropanoate compound of formula-8a (100 gm) and isopropyl alcohol (200 ml) at 25-30° C. and stirred for 2 hrs at the same temperature. Filtered the precipitated solid, washed with methyl tert.butyl ether and then dried the material to get the title compound.

Yield: 63.0 gm; M.R: 190-196° C.; Purity by HPLC: 98.5%.

Example-12: Preparation of (S)-methyl 2-((S)-2-tert.butoxycarbonylamino-4-phenylbutanamido-4-methylpentanamido)-3-phenyl propanoate (Formula-11a)

Hydroxybenzotriazole (7.3 gm) and N-methylmorpholine (55.2 gm) were slowly added to a pre-cooled mixture of (S)-methyl 2-((S)-2-amino-4-methylpentanamido)-3-phenylpropanoate hydrochloride compound of formula-9a (90 gm), (S)-2-(tert-butoxycarbonylamino)-4-phenylbutanoic acid compound of formula-10a (84.2 gm) and dichloromethane (630 ml) at 0-5° C. under nitrogen atmosphere. A solution of dicyclohexylcarbodiimide (67.5 gm) in dichloromethane (270 ml) was slowly added to the reaction mixture at 0-5° C. Raised the temperature of the reaction mixture to 25-30° C. and stirred for 2 hrs at the same temperature. Filtered the reaction mixture and cooled the filtrate to 10-15° C. The filtrate was washed with aqueous sodium bicarbonate solution followed by with aqueous hydrochloric acid solution and then with water. Distilled off the solvent completely from the reaction mixture under reduced pressure. Isopropyl alcohol (1350 ml) was added to the obtained solid. Heated the reaction mixture to 75-80° C. and stirred for 1 hr at the same temperature. Cooled the reaction mixture to 25-30° C. and stirred for 1 hr at the same temperature. Filtered the solid, washed with methyl tert.butyl ether and then dried to get the title compound.

Yield: 121.0 g; M.R: 110-120° C.

Example-13: Preparation of (S)-methyl 2-((S)-2-((S)-2-amino-4-phenylbutanamido)-4-methylpentanamido)-3-phenylpropanoate hydrochloride (Formula-12a)

Ethyl acetate-HCl (1000 ml) was slowly added to a mixture of (S)-methyl 2-((S)-2-tert.butoxycarbonylamino-4- phenylbutanamido-4-methylpentanamido)-3-phenyl propanoate compound of formula-11a (100 gm) and ethyl acetate (300 ml) at 25-30° C. and stirred for 2 hrs at the same temperature. Filtered the precipitated solid, washed with methyl tert.butyl ether and then dried the material to get the title compound.

Yield: 75.2 gm; M.R: 250-255° C.

Example-14: Preparation of (S)-2-((S)-4-methyl-2-((S)-2-(2-morpholinoacetamido)-4-phenylbutanamido)pentanamido)-3-phenylpropanoic acid (Formula-2)

Hydroxybenzotriazole (4.1 gm) and N-methylmorpholine (31 gm) were added to a pre-cooled mixture of (S)-methyl 2-((S)-2-((S)-2-amino-4-phenylbutanamido)-4-methylpentanamido)-3-phenylpropanoate hydrochloride compound of formula-12a (75 gm), 2-morpholinoacetic acid hydrochloride compound of formula-13a (30.4 gm) and dichloromethane (525 ml) at 0-5° C. under nitrogen atmosphere. A solution of dicyclohexylcarbodiimide (37.9 gm) in dichloromethane (225 ml) was slowly added to the reaction mixture at 0-5° C. Raised the temperature of the reaction mixture to 25-30° C. and stirred for 2 hrs at the same temperature. Filtered the reaction mixture, cooled the filtrate to 10-15° C. and washed with aqueous sodium bicarbonate solution followed by with aqueous hydrochloric acid solution and then with water. Distilled off the solvent completely from the reaction mixture under reduced pressure. Tetrahydrofuran (750 ml) and water (375 ml) were added to the obtained solid at 25-30° C. Cooled the reaction mixture to 10-15° C. and aqueous LiOH.H$_2$O solution (12.8 gm of LiOH.H$_2$O dissolved in 75 ml of water) was added. Raised the temperature of the reaction mixture to 25-30° C. and stirred for 3 hrs at the same temperature. Water and dichloromethane were added to the reaction mixture at 25-30° C. and stirred for 10 min at the same temperature. Both the organic and aqueous layers were separated and the aqueous layer was washed with dichloromethane. Acidified the aqueous layer using aq.hydrochloric acid solution at 25-30° C. and stirred the reaction mixture for 30 min at the same temperature. Filtered the precipitated solid and washed with water. Methanol (450 ml) was added to the obtained solid at 25-30° C. Heated the reaction mixture to 55-60° C. and stirred for 30 min at the same temperature. Ethanol (225 ml) was added to the reaction mixture at 55-60° C. and stirred for 45 min at the same temperature. Cooled the reaction mixture to 25-30° C. and stirred for 1 hr at the same temperature. Filtered the precipitated solid, washed with methanol and then dried the material to get the title compound.

Yield: 48.0 gm; M.R: 208-215° C.

Example-15: Preparation of (S)-perfluorophenyl 2-((S)-4-methyl-2-((S)-2-(2-morpholino acetamido)-4-phenylbutanamido)pentanamido)-3-phenylpropanoate (Formula-3a)

1-[bis(dimethylamino)methylene]-1H-1,2,3-triazolo[4,5-b]pyridinium 3-oxid hexafluorophosphate (HATU; 1.48 gm) and N-methylmorpholine (0.7 gm) were added to a pre-cooled mixture of (S)-2-((S)-4-methyl-2-((S)-2-(2-morpholinoacetamido)-4-phenyl butanamido)pentanamido)-3-phenylpropanoic acid compound of formula-2 (2 gm) and dichloromethane (20 ml) at 0-5° C. under nitrogen atmosphere. A solution of 2,3,4,5,6-pentafluoro phenol (0.58 gm) in dichloromethane (5 ml) was slowly added to the reaction mixture at 0-5° C. and stirred for 6 hrs at the same temperature. Aqueous sodium bicarbonate solution was slowly added to the reaction mixture at 0-5° C. and raised the temperature of the reaction mixture to 25-30° C. Filtered the reaction mixture, both the organic and aqueous layers were separated from the filtrate and the organic layer was washed with water. Silica gel (10 gm) was added to the organic layer and stirred the reaction mixture for 30 min. Filtered the reaction mixture and washed the silica gel with dichloromethane. Distilled off the solvent completely from the filtrate under reduced pressure. n-Heptane (10 ml) was added to the obtained compound at 25-30° C. and stirred the reaction mixture for 2 hrs at the same temperature. Filtered the solid, washed with n-heptane and then dried the material to get the tile compound.

Yield: 1.8 gm.

Example-16: Preparation of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenyl butanamido)-4-methylpentanamide (Formula-1)

A mixture of (S)-2-amino-4-methyl-1-((R)-2-methyloxiran-2-yl)pentan-1-one trifluoroacetic acid salt compound of formula-4a (0.37 gm), sodium carbonate (0.43 ml) and dichloromethane (5 ml) was stirred for 20 min at 25-30° C. under nitrogen atmosphere. Filtered the reaction mixture, and the filtrate was added to a mixture of (S)-perfluorophenyl 2-((S)-4-methyl-2-((S)-2-(2-morpholinoacetamido)-4-phenylbutanamido)pentanamido)-3-phenylpropanoate compound of formula-3a (1 gm), dichloromethane (10 ml) and triethylamine (0.21 ml) at 25-30° C. and stirred the reaction mixture for 6 hrs at the same temperature. Aqueous sodium bicarbonate solution was slowly added to the reaction mixture and stirred for 10 min. Both the organic and aqueous layers were separated and the organic layer was washed with water. Distilled off the solvent completely from the organic layer under reduced pressure. Methanol (16 ml) and water (8 ml) were added to the obtained compound at 25-30° C. and stirred the reaction mixture for 2 hrs at the same temperature. Filtered the solid, washed with water and then dried the material. The obtained compound is purified by preparative HPLC by using acetonitrile/water as eluent to get pure title compound.

Yield: 0.5 gm; Purity by HPLC: 99.9%.

Example-17: Preparation of Amorphous Form of Compound of Formula-1

Dichloromethane (400 ml) was added to (2S)-N-((S)-1-((S)-4-methyl-1-((R)-2-methyloxiran-2-yl)-1-oxopentan-2-ylcarbamoyl)-2-phenylethyl)-2-((S)-2-(2-morpholino acetamido)-4-phenylbutanamido)-4-methylpentanamide compound of formula-1 (100 gm) at 25-30° C. under nitrogen atmosphere and stirred for 10 min. Distilled off the solvent completely from the reaction mixture under reduced pressure to get the title compound.

Yield: 98.0 gm; Purity by HPLC: 99.9%.

Example-18: Preparation of (S)-methyl 2-amino-3-phenylpropanoate hydrochloride (Formula-6a)

Thionyl chloride (216 gm) was slowly added to a mixture of (S)-2-amino-3-phenylpropanoic acid compound of formula-5 (200 gm) and methanol (1000 ml) at 25-30° C. and the obtained reaction mixture was stirred for 8 hrs at 45-50°

C. Distilled off the solvent and excess thionyl chloride from the reaction mixture under reduced pressure. Cooled the reaction mixture to 25-30° C., methyl tert.butyl ether (800 ml) was added and stirred for 1 hr at the same temperature. Filtered the solid, washed with methyl tert.butyl ether and dried to get the title compound.

Yield: 256.5 gm; M.R: 151-157° C.; Purity by HPLC: 99.9%.

Example-19: Preparation of (S)-methyl 2-((S)-2-amino-4-methylpentanamido)-3-phenylpropanoate hydrochloride (Formula-9a)

Hydroxybenzotriazole (10.8 gm) followed by N-methylmorpholine (81.2 gm) were added to a pre-cooled mixture of (S)-methyl 2-amino-3-phenylpropanoate hydrochloride compound of formula-6a (86.2 gm), (S)-2-(tert-butoxycarbonylamino)-4-methylpentanoic acid compound of formula-7a (100 gm) and dichloromethane (700 ml) at 0-5° C. under nitrogen atmosphere. A solution of dicyclohexylcarbodiimide (99.2 gm) in dichloromethane (300 ml) was slowly added to the reaction mixture at 0-5° C. Raised the temperature of the reaction mixture to 25-30° C. and stirred for 2 hrs at the same temperature. Filtered the reaction mixture and cooled the filtrate to 10-15° C. Washed the filtrate with aqueous sodium bicarbonate solution followed by with water. Distilled off the solvent completely from the reaction mixture under reduced pressure. Isopropyl alcohol (200 ml) was added to the obtained compound at 25-30° C. Isopropyl alcohol-HCl (1300 ml) was added to the reaction mixture at 25-30° C. and stirred the reaction mixture for 2 hrs at the same temperature. Filtered the precipitated solid, washed with methyl tert.butyl ether and dried the material to get the title compound.

Yield: 81.0 gm; M.R: 190-196° C.

Example-20: Preparation of (S)-methyl 2-((S)-2-((S)-2-amino-4-phenylbutanamido)-4-methylpentanamido)-3-phenylpropanoate hydrochloride (Formula-12a)

Hydroxybenzotriazole (4.5 gm) followed by N-methylmorpholine (33.8 gm) were added to a pre-cooled mixture of (S)-methyl 2-((S)-2-amino-4-methylpentanamido)-3-phenylpropanoate hydrochloride compound of formula-9a (55 gm), (S)-2-(tert-butoxycarbonylamino)-4-phenylbutanoic acid compound of formula-10a (51.3 gm) and dichloromethane (385 ml) at 0-5° C. under nitrogen atmosphere. A solution of dicyclohexylcarbodiimide (41.3 gm) in dichloromethane (165 ml) was slowly added to the reaction mixture at 0-5° C. Raised the temperature of the reaction mixture to 25-30° C. and stirred for 2 hrs at the same temperature. Filtered the reaction mixture and cooled the filtrate to 10-15° C. Washed the filtrate with aqueous sodium bicarbonate solution followed by with water. Distilled off the solvent completely from the reaction mixture under reduced pressure. Isopropyl alcohol (825 ml) was added to the obtained compound at 25-30° C. Heated the reaction mixture to 80-85° C. and stirred for 1 hr at the same temperature. Cooled the reaction mixture to 25-30° C. and stirred the reaction mixture for 1 hr at the same temperature. Filtered the solid, washed with methyl tert.butyl ether. Ethyl acetate (220 ml) was added to the obtained solid at 25-30° C. Ethyl acetate-HCl (715 ml) was slowly added to the reaction mixture at 25-30° C. and stirred the reaction mixture for 2 hrs at the same temperature. Filtered the precipitated solid, washed with methyl tert.butyl ether and then dried to get the title compound.

Yield: 58.0 gm; M.R: 235-241° C.

Example-21: Preparation of (S)-2-((S)-4-methyl-2-((S)-2-(2-morpholinoacetamido)-4-phenylbutanamido)pentanamido)-3-phenylpropanoic acid (Formula-2)

Hydroxybenzotriazole (4.1 gm) followed by N-methylmorpholine (31 gm) were added to a pre-cooled mixture of (S)-methyl 2-((S)-2-((S)-2-amino-4-phenylbutanamido)-4-methylpentanamido)-3-phenylpropanoate hydrochloride compound of formula-12a (75 gm), 2-morpholinoacetic acid hydrochloride compound of formula-13a (30.4 gm) and dichloromethane (525 ml) at 0-5° C. under nitrogen atmosphere. A solution of dicyclohexylcarbodiimide (37.9 gm) in dichloromethane (225 ml) was slowly added to the reaction mixture at 0-5° C. Slowly raised the temperature of the reaction mixture to 25-30° C. and stirred for 2 hrs at the same temperature. Filtered the reaction mixture and cooled the filtrate to 10-15° C. Washed the filtrate with aqueous sodium bicarbonate solution followed by aqueous hydrochloric acid solution and then with water. Distilled off the solvent completely from the reaction mixture under reduced pressure. Tetrahydrofuran (750 ml) followed by water (375 ml) were added to the obtained compound at 25-30° C. and cooled the reaction mixture to 10-15° C. A solution of lithium hydroxide monohydrate (12.9 gm) in water (75 ml) was added to the reaction mixture at 10-15° C. Raised the temperature of the reaction mixture to 25-30° C. and stirred for 3 hrs at the same temperature. Water and dichloromethane were added to the reaction mixture at 25-30° C. and stirred for 5 min. Both the organic and aqueous layers were separated and washed the aqueous layer with dichloromethane. Acidified the aqueous layer with aqueous hydrochloric acid solution at 25-30° C. and stirred the reaction mixture for 1 hr at the same temperature. Filtered the precipitated solid and washed with water. Methanol (450 ml) was added to the obtained solid at 25-30° C. Heated the reaction mixture to 55-60° C. and stirred for 45 min at the same temperature. Cooled the reaction mixture to 25-30° C. and stirred for 1 hr at the same temperature. Filtered the solid, washed with methanol and dried to get the title compound.

Yield: 47.6 gm; M.R: 209-210° C.

Example-22: Preparation of (S)-2,5-dioxopyrrolidin-1-yl 2-((S)-4-methyl-2-((S)-2-(2-morpholinoacetamido)-4-phenylbutanamido)pentanamido)-3-phenylpropanoate (Formula-3b)

A solution of diisopropyl carbodiimide (6.12 gm) in dichloromethane (75 ml) was slowly added to a mixture of (S)-2-((S)-4-methyl-2-((S)-2-(2-morpholinoacetamido)-4-phenylbutanamido)pentanamido)-3-phenylpropanoic acid compound of formula-2 (25 gm), N-hydroxysuccinimide (5.6 gm) and dichloromethane (250 ml) at 25-30° C. under nitrogen atmosphere and stirred the reaction mixture for 4 hrs at the same temperature. Cooled the reaction mixture to 0-5° C. and stirred for 2 hrs at the same temperature. Filtered the reaction mixture and distilled off the solvent completely from the filtrate under reduced pressure to get the title compound as a solid.

Yield: 26.5 gm.

Example-23: Preparation of (S)-2-(tert-butoxycarbonylamino)-4-methylpentanoic acid monohydrate (S)-2-Amino-4-methyl pentanoic acid (100 gm) was added to a solution of sodium hydroxide (36.6 gm) in water (800 ml) at 25-30° C. and stirred the reaction mixture for 15 min at the same temperature. Di-tert-butyl dicarbonate (200 gm) was slowly added to the reaction mixture lot wise at 25-30° C. and stirred the reaction mixture for 20 hrs at the same temperature. Acidified the reaction mixture using aqueous hydrochloric acid solution at 25-30° C. and stirred for 30 min at the same temperature. Filtered the precipitated solid and washed with water. Methanol (300 ml) was added to the obtained solid at 25-30° C. and stirred the reaction mixture for 15 min at the same temperature. Water (500 ml) was slowly added to the reaction mixture at 25-30° C. and stirred for 1 hr at the same temperature. Filtered the precipitated solid, washed with water and dried to get the title compound.

Yield: 155.0 gm.

Example-24: Preparation of (S)-tert-butyl 1-(methoxy(methyl)amino)-4-methyl-1-oxopentan-2-ylcarbamate N-Methylmorpholine (55.1 ml) was added to a pre-cooled solution of (S)-2-(tert-butoxycarbonylamino)-4-methylpentanoic acid monohydrate (50 gm) in dichloromethane (350 ml) at −10° C. to −15° C. under nitrogen atmosphere. Ethyl chloroformate (22.9 ml) was slowly added to the reaction mixture at −10° C. to −15° C. and stirred for 20 min at the same temperature. N,O-dimethylhydroxylamine hydrochloride (23.5 gm) was slowly added to the reaction mixture at −10° C. to −15° C. and stirred for 2 hrs at the same temperature. Raised the temperature of the reaction mixture to 0-5° C., quenched the reaction mixture with water and stirred for 15 min at the same temperature. Both the organic and aqueous layers were separated and washed the organic layer with 10% aqueous sodium bicarbonate solution. Distilled off the solvent completely from the organic layer under reduced pressure to get the title compound.

Yield: 48.0 gm.

Example-25: Preparation of (S)-tert-butyl 2,6-dimethyl-3-oxohept-1-en-4-ylcarbamate A mixture of magnesium (24 gm), iodine (0.5 gm) and tetrahydrofuran (1000 ml) was heated to 50-55° C. under nitrogen atmosphere. A solution of 2-bromo propene (123.5 gm) in tetrahydrofuran (250 ml) was slowly added lot wise to the reaction mixture at 50-55° C. and stirred the reaction mixture for 2 hrs 30 min at the same temperature. Cooled the reaction mixture to 25-30° C. and the resulting reaction mixture was added to a pre-cooled mixture of (S)-tert-butyl 1-(methoxy(methyl)amino)-4-methyl-1-oxopentan-2-ylcarbamate (50 gm) and tetrahydrofuran at 0-5° C. and stirred the reaction mixture for 15 min at the same temperature. Raised the temperature of the reaction mixture to 25-30° C. and stirred for 8 hrs at the same temperature. The obtained reaction mixture was slowly added to a pre-cooled mixture of water and ammonium chloride at 0-5° C. and stirred for 30 min at the same temperature. Neutralized the reaction mixture using aqueous hydrochloric acid solution and stirred the reaction mixture for 15 min. Both the organic and aqueous layers were separated and the aqueous layer was extracted with ethyl acetate. Combined the organic layers and distilled off the solvent completely under reduced pressure. Dichloromethane was added to the obtained compound at 25-30° C. and stirred for 5 min. Silica gel was added to the reaction mixture and distilled off the solvent completely from the reaction mixture. Cooled the obtained compound to 25-30° C., cyclohexane (247.5 ml) and ethyl acetate (2.5 ml) were added and stirred the reaction mixture for 45 min at the same temperature. Filter the reaction mixture and distill off the solvent completely from the filtrate under reduced pressure to get the title compound.

Yield: 38.5 gm.

Example-26: Preparation of tert-butyl (S)-4-methyl-1-((R)-2-methyloxiran-2-yl)-1-oxopentan-2-ylcarbamate (Formula-15)

A mixture of (S)-tert-butyl 2,6-dimethyl-3-oxohept-1-en-4-ylcarbamate (50 gm), methanol (1250 ml) and potassium carbonate (13.5 gm) was stirred for 15 min at 25-30° C. Benzonitrile (10.1 gm) was added to the reaction mixture and cooled to 0-5° C. 50% hydrogen peroxide (1.6 gm) was slowly added to the reaction mixture at 0-5° C. and raised the temperature of the reaction mixture to 25-30° C. Second lot of 50% hydrogen peroxide (25 gm) was slowly added to the reaction mixture at 25-30° C. and stirred for 6 hrs at the same temperature. The obtained reaction mixture was slowly added to a pre-cooled solution of sodium thiosulfate and water at 0-5° C. and stirred the reaction mixture for 20 min at the same temperature. Raised the temperature of the reaction mixture to 25-30° C., dichloromethane was added and stirred for 15 min at the same temperature. Both the organic and aqueous layers were separated and the organic layer was washed with aqueous sodium thiosulfate solution. Distilled off the solvent completely from the organic layer under reduced pressure and the obtained compound was purified by column chromatography using ethyl acetate:cyclohexane as eluent.

Yield: 16.5 gm.

Example-27: Preparation of Compound of Formula-1

Tert-butyl (S)-4-methyl-1-((R)-2-methyloxiran-2-yl)-1-oxopentan-2-ylcarbamate compound of formula-15 (10 gm) was added to a solution of trifluoroacetic acid (30 ml) in dichloromethane (70 ml) at 5-10° C. under nitrogen atmosphere and stirred the reaction mixture for 3 hrs at the same temperature. Distilled off the solvent completely from the reaction mixture and the residue obtained was dissolved in dichloromethane. Aqueous sodium carbonate solution was added to the reaction mixture at 25-30° C. and stirred for 20 min at the same temperature. Filtered the reaction mixture and both the organic and aqueous layers were separated from the filtrate. (S)-2,5-dioxopyrrolidin-1-yl 2-((S)-4-methyl-2-((S)-2-(2-morpholinoacetamido)-4-phenylbutanamido)pentanamido)-3-phenylpropanoate compound of formula-3b (25 gm) and dichloromethane (120 ml) were added to the above organic layer and stirred the reaction mixture for 60 min at the same temperature. Water was added to the reaction mixture and stirred for 5 min. Both the organic and aqueous layers were separated and the aqueous layer was extracted with dichloromethane. Combined the organic layers and washed with 5% aqueous sodium bicarbonate solution followed by with 5% aqueous sodium chloride solution. Distilled off the solvent completely from the organic layer under reduced pressure and purified the obtained compound by column chromatography using methanol:dichloromethane as eluent to get the title compound. The obtained compound was purified by preparative HPLC using acetonitrile:water as eluent.

Yield: 19.0 gm.

Example-28: Preparation of (S)-perfluorophenyl 2-((S)-4-methyl-2-((S)-2-(2-morpholino acetamido)-4-phenylbutanamido)pentanamido)-3-phenylpropanoate (Formula-3a)

1-[Bis(dimethylamino)methylene]-1H-1,2,3-triazolo[4,5-b]pyridinium 3-oxid hexafluorophosphate (22.3 gm) and hydroxybenzotriazole (1.4 gm) were added to a pre-cooled mixture of (S)-2-((S)-4-methyl-2-((S)-2-(2-morpholinoacetamido)-4-phenyl butanamido)pentanamido)-3-phenylpropanoic acid (30 gm) and dichloromethane (300 ml) at 10-15° C. under nitrogen atmosphere. A solution of 2,3,4,5,6-pentafluorophenol (11.7 gm) in dichloromethane (90 ml) was added to the reaction mixture at 10-15° C. A solution of N-methylmorpholine (6.4 gm) in dichloromethane (60 ml) was slowly added to the reaction mixture at 10-15° C. and stirred for 45 min at the same temperature. Aqueous sodium bicarbonate solution was added to the reaction mixture at 10-15° C. and stirred for 5 min at the same temperature. Filtered the reaction mixture, both the organic and aqueous layers were separated and washed the organic layer with water. Silica was added to the organic layer and stirred for 10 min. Filtered the reaction mixture through hyflow bed and washed the hyflow bed with dichloromethane. Distilled off the solvent completely from the organic layer and co-distilled with methyl tert.butyl ether. 180 ml of methyl tert.butyl ether was added to the obtained solid at 25-30° C. and stirred the reaction mixture for 40 min at the same temperature. Filtered the solid, washed with methyl tert.butyl ether and then dried the material to get title compound.
Yield: 27.0 gm; M.R: 155-162° C.

Example-29: Preparation of Compound of Formula-1

Tert-butyl (S)-4-methyl-1-((R)-2-ethyloxirane-2-yl oxopentan-2-ylcarbamate compound of formula-15 (37 gm) was added to a pre-cooled mixture of trifluoroacetic acid (92.3 gm) and dichloromethane (300 ml) at 0-5° C. and stirred the reaction mixture for 3 hrs at the same temperature. Distilled off the solvent completely from the reaction mixture under reduced pressure. The obtained compound was dissolved in dichloromethane (300 ml) at 25-30° C. Cooled the reaction mixture to 10-15° C., sodium carbonate (43.4 gm) was slowly added and stirred for 10 min at the same temperature. Filtered the reaction mixture and the filtrate was added to a solution of (S)-perfluorophenyl 2-((S)-4-methyl-2-((S)-2-(2-morpholinoacetamido)-4-phenyl butanamido)pentanamido)-3-phenylpropanoate compound of formula-3a (100 gm) in dichloromethane (300 ml) at 25-30° C. and stirred the reaction mixture for 3 hrs at the same temperature. Water was added to the reaction mixture at 25-30° C. and stirred for 10 min at the same temperature. Both the organic and aqueous layers were separated and distilled off 60% of solvent from the organic layer under reduced pressure. The obtained solution was charged into a column loaded with silica gel. Run the column initially with dichloromethane and the product was eluted with dichloromethane:methanol (9:1) as eluent. The pure fractions were collected and distilled off the solvent under reduced pressure to get the title compound as solid. The obtained compound was purified by preparative HPLC using acetonitrile:water as eluent.
Yield: 58.0 gm.

Example-30: Preparation of Compound of Formula-1

(S)-2-Amino-4-methyl-1-((R)-2-methyloxiran-2-yl)pentan-1-one trifluoroacetic acid salt compound of formula-4a (47 gm) was added to a pre-cooled solution of (S)-2-((S)-4-methyl-2-((S)-2-(2-morpholinoacetamido)-4-phenylbutanamido)pentanamido)-3-phenyl propanoic acid compound of formula-2 (100 gm) and N,N-dimethylformamide (1000 ml) at 0-5° C. under nitrogen atmosphere. 1-[bis(dimethylamino)methylene]-1H-1,2,3-triazolo[4,5-b]pyridinium 3-oxid hexafluoro phosphate (74 gm), hydroxybenzotriazole (4 gm) and N-methylmorpholine (38.4 ml) were added to the reaction mixture at 0-5° C. and stirred for 3 hrs at the same temperature. Aqueous sodium bicarbonate solution and ethyl acetate were added to the reaction mixture at 10-15° C. and stirred for 10 min at the same temperature. Both the organic and aqueous layers were separated and extracted the aqueous layer with ethyl acetate. Combined the organic layers and washed with water. Distilled off the solvent completely from the organic layer under reduced pressure. Methanol (800 ml) was added to the obtained compound at 25-30° C. Heated the reaction mixture to 55-60° C. and water (800 ml) was added at the same temperature. Cooled the reaction mixture to 25-30° C. and stirred for 2 hrs at the same temperature. Filtered the precipitated solid, washed with water and then dried the material to get pure title compound.
Yield: 100.0 gm.

We claim:
1. A process for the preparation of Carfilzomib of formula-1, comprising:

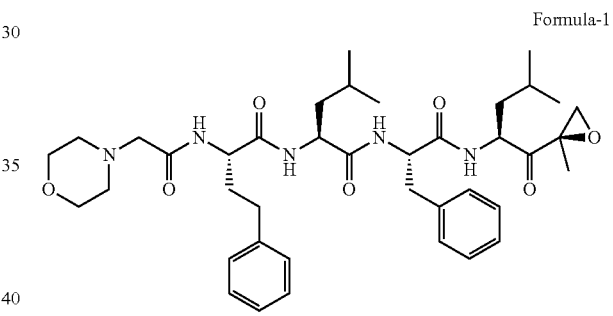

Formula-1 a) reacting the (S)-2-((S)-4-methyl-2-((S)-2-(2-morpholinoacetamido)-4-phenyl butanamido)pentanamido)-3-phenylpropanoic acid compound of formula-2

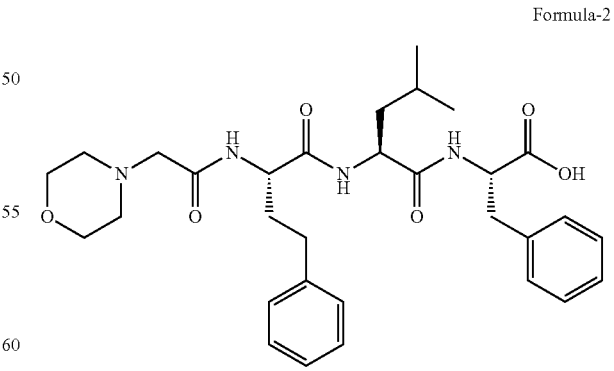

Formula-2 with compound of general formula $R_1$—OH in a solvent in presence of 1-[bis(dimethylamino)methylene]-1H-1,2,3-triazolo[4,5-b]pyridinium 3-oxid hexafluorophosphate (HATU) and/or base to obtain compound of general formula-3, Formula-3

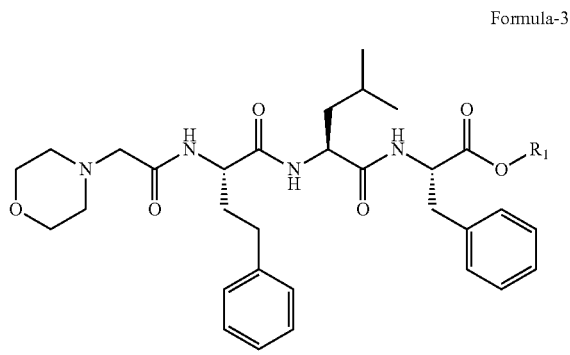

wherein, 'R₁' represents substituted/unsubstituted C₆-C₁₀ aryl/aralkyl group; aliphatic group such as alkylsulfonyls; substituted/unsubstituted aryl sulfonyl; aromatic groups such as substituted/unsubstituted aryl/aralkyl having one or more similar or different substituents selected from hydroxy, halogens, NO₂, NH₂, alkylamino, arylamino, alkoxy, aryloxy, cyano, sulfonic acid, SCH₃, SO₂CH₃, SO₂NH₂; and

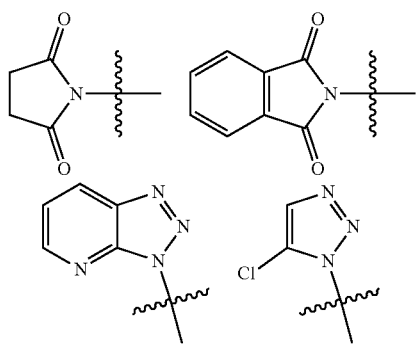

b) optionally isolating the compound of general formula-3 from the reaction mixture as a solid, c) reacting the compound of general formula-3 with (S)-2-amino-4-methyl-1-((R)-2-methyloxiran-2-yl)pentan-1-one compound of formula-4 or its acid-addition salt Formula-4

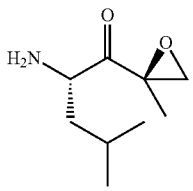

in a solvent optionally in presence of a base to obtain compound of formula-1.

2. The process according to claim 1, wherein
in step a) and step c) the solvent wherever necessary is selected from hydrocarbon solvents, ether solvents, ester solvents, polar-aprotic solvents, chloro solvents, ketone solvents, nitrile solvents, alcohol solvents, polar solvents or their mixtures; and
in step-a) & step-b) the base is selected from organic bases, inorganic bases.

3. The process according to claim 1, wherein the process further comprises preparation of (S)-perfluorophenyl 2-((S)-4-methyl-2-((S)-2-(2-morpholinoacetamido)-4-phenylbutanamido)pentanamido)-3-phenylpropanoate, comprising reacting the (S)-2-((S)-4-methyl-2-((S)-2-(2-morpholinoacetamido)-4-phenylbutanamido)pentanamido)-3-phenylpropanoic acid compound of formula-2 with 2,3,4,5,6-pentafluoro phenol in a solvent optionally in presence of coupling agent and/or a base.

4. The process according to claim 3, wherein the compound of formula-3a is obtained as solid.

5. A process for the preparation of (2S)-N-((S)-1-((S)-4-methyl-1-((R)-2-methyloxiran-2-yl)-1-oxopentan-2-ylcarbamoyl)-2-phenylethyl)-2-((S)-2-(2-morpholino acetamido)-4-phenylbutanamido)-4-methylpentanamide compound of formula-1, comprising reacting the compound of general formula-3, Formula-3

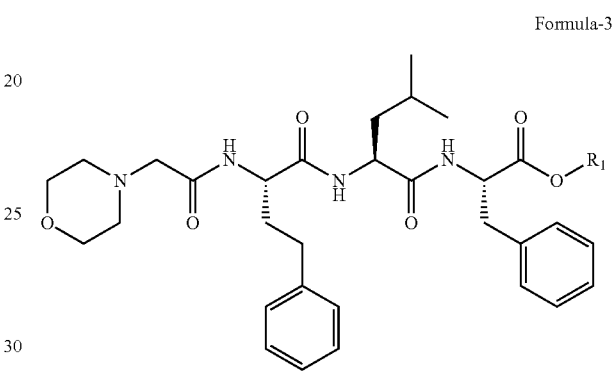

wherein, 'R₁' represents substituted/unsubstituted C₆-C₁₀ aryl/aralkyl group; aliphatic group such as alkylsulfonyls; substituted/unsubstituted arylsulfonyl; aromatic groups such as substituted/unsubstituted aryl/aralkyl having one or more similar or different substituents selected from hydroxy, halogens, NO₂, NH₂, alkylamino, arylamino, alkoxy, aryloxy, cyano, sulfonic acid, SCH₃, SO₂CH₃, SO₂NH₂; and

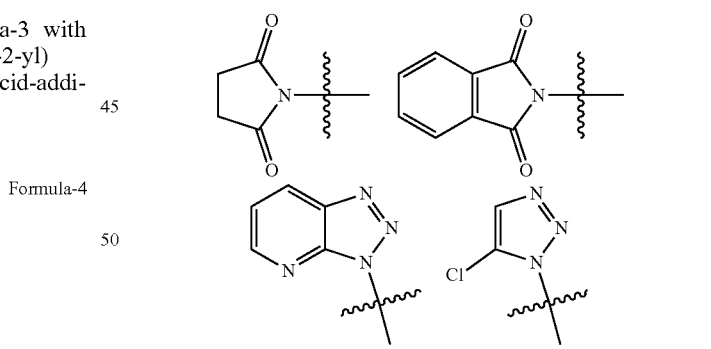

with (S)-2-amino-4-methyl-1-((R)-2-methyloxiran-2-yl)pentan-1-one compound of formula-4

Formula-4

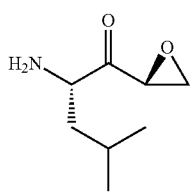

or its salt in a solvent optionally in presence of a base to obtain compound of formula-1

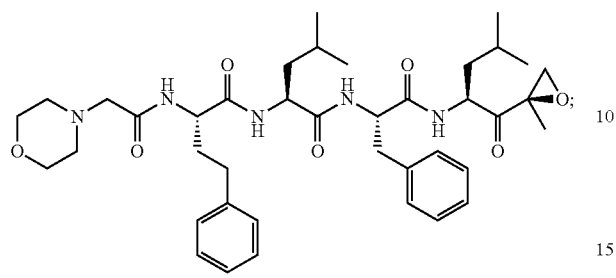

Formula-1 wherein the base is selected from organic bases, inorganic bases and the solvent is selected from hydrocarbon solvents, ether solvents, ester solvents, polar-aprotic solvents, chloro solvents, ketone solvents, nitrile solvents, alcohol solvents, polar solvents or their mixtures.

* * * * *